(12) United States Patent
Henkelmann et al.

(10) Patent No.: US 6,710,157 B2
(45) Date of Patent: Mar. 23, 2004

(54) POLYCARBAMATES AND METHOD FOR THE PRODUCTION THEREOF

(75) Inventors: Jochem Henkelmann, Mannheim (DE); Heiko Maas, Mannheim (DE); Armin Stamm, Nieder-Olm (DE); Heinz-Peter Rink, Muenster (DE); Werner-Alfons Jung, Ascheberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/363,674

(22) PCT Filed: Aug. 30, 2001

(86) PCT No.: PCT/EP01/10030

§ 371 (c)(1),
(2), (4) Date: Mar. 6, 2003

(87) PCT Pub. No.: WO02/20468

PCT Pub. Date: Mar. 14, 2002

(65) Prior Publication Data

US 2003/0176727 A1 Sep. 18, 2003

(30) Foreign Application Priority Data

Sep. 7, 2000 (DE) .......................................... 100 44 165

(51) Int. Cl.$^7$ ................................................. C08G 6/00
(52) U.S. Cl. ........................... 528/196; 560/24; 560/25; 560/158
(58) Field of Search .......................... 528/196; 560/24, 560/25, 158

(56) References Cited

U.S. PATENT DOCUMENTS 4,415,745 A  *  11/1983  Ryu et al. .................... 560/25
5,453,536 A  *  9/1995   Dai et al. .................... 560/345

FOREIGN PATENT DOCUMENTS

| DE | 196 54 167 | 6/1998 |
|----|-----------|--------|
| EP | 0 594 068 | 4/1994 |
| EP | 0 767 230 | 4/1997 |

* cited by examiner

Primary Examiner—Terressa Boykin
(74) Attorney, Agent, or Firm—Oblon, Spivak, McClelland, Maier & Neustadt, P.C.

(57) ABSTRACT

The invention relates to polycarbamates of the formula I

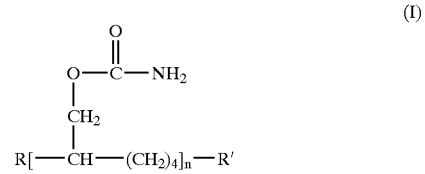

in which

R and R' are identical or different and are alkyl groups having 1–4 carbon atoms and n is a number from, on average, 2 to 5.

7 Claims, No Drawings

POLYCARBAMATES AND METHOD FOR THE PRODUCTION THEREOF

The invention relates to aliphatic polycarbamates and to a process for their preparation.

Aliphatic polycarbamates, i.e. carbamates having more than one, preferably more than two, carbamates groups in the molecule, are known and are used inter alia as crosslinkers for the manufacture of automotive finishes. Since it is desired to lower the solvent content of coatings to reduce emissions, it is necessary, in order to retain a viscosity which is sufficiently low for application of the coating, to have available coating constituents of low viscosity.

EP-A 0 594 068 discloses a curable composition comprising a polycarbamate of the formula A

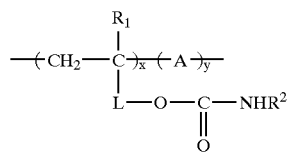

where $R^1$=H or $CH_3$, $R^2$=H, alkyl or cycloalkyl, L=a divalent linking group, A=a repeat unit derived from an ethylenically unsaturated monomer, x=10–90% by weight y=10–90% by weight and x+y=100% by weight.

It is an object of the present invention to provide novel aliphatic polycarbamates which, while being of low viscosity, contain two or more carbamate groups in the molecule, and whose molecular size and number of carbamate groups can be varied as desired, and also a process for their preparation.

We have found that this object is achieved by polycarbamates of the formula I

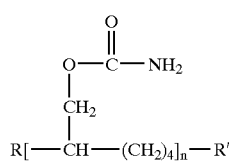

in which

R and R' are identical or different and are alkyl groups having 1–4 carbon atoms and n is a number from, on average, 2 to 5.

The invention further provides a process for the preparation of polycarbamates of the formula I, which consists in reacting a polyalcohol of the formula II

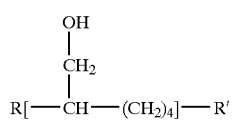

wherein R, R' and n are as defined above, with phosgene, preferably in excess, to give a polychlorocarbonic ester of the formula III

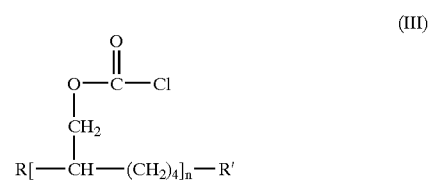

The polychlorocarbonic ester III is then converted to the polycarbamate I using ammonia.

Within the context of this description, polycarbamates and polyalcohols are understood as meaning those compounds which—in any case on average in the case of homolog mixtures—contain more than 2 carbamate or OH groups, i.e. essentialy those representatives which can be referred to as oligomers. The polycarbamates according to the invention are frequently in the form of mixtures of homologs which primarily contain representatives where n=1 to approximately n=10.

The amination is generally carried out at a temperature of from 5 to 50° C., preferably at 25 to 30° C., and at a pressure of from 1 to 10 bar, preferably 1 to 3 bar. Here, it is possible to work in an inert solvent, such as toluene, chlorobenzene, heptane, dichloroethane and pentyl acetate. Preferably, the amination of the polychlorocarbonic esters is carried out without the addition of an inert solvent.

The compounds of the formula II are known and are described, for example, in DE-A 196 54 167. They are preferably obtained by catalyzed methathesis reaction of cyclopentene-containing hydrocarbon mixtures, for example petroleum fractions, hydroformylation of the reaction products and subsequent reaction with hydrogen over a hydrogenation catalyst.

The reaction of the polyalcohols with phosgene is generally carried out at a temperature of from +5 to 65° C., particularly advantageously at a temperature of from +40° C. to 45° C. The phosgene is generally allowed to act in an excess of from 5 to 20 mol %, meaning that normally virtually all pi hydroxyl groups are converted to chloroformate groups.

The reaction of the polyalcohols can be carried out without the addition of inert solvents. However, it is generally advantageous to work in an aprotic solvent such as toluene.

The polycarbamates according to the invention are used as coating constituents, in particular in automotive finishes, where they are added to regulate the viscosity.

The examples below describe preferred embodiments of the invention. The OH numbers given therein signify g of OH per 100 g of substance. Determination of the OH number is described in DE-A 196 54 167.

EXAMPLE 1

Preparation of the polychlorocarbonic ester III

A 0.51 capacity glass stirred flask with gas inlet pipe and a brine cooler of −15° C. and a dry ice cooler was charged with 50 g of toluene and, at 40–45° C., 80 g of phosgene were introduced until reflux occurred. To this, over the course of 7 hours, 150 g of polyhydric alcohol corresponding to the formula II in 50 g of toluene having an OH number of 359 and a further 135 g of phosgene were added. The mixture was then after-stirred for 2 hours at 40 to 45° C. Then, at 40–45° C., nitrogen was passed through the reaction mixture until all of the phosgene had been removed, 197 g of chloroformate III were obtained. The alcohol conversion was quantitative.

EXAMPLE 2

Preparation of the polycarbamate I

In a 0.51 glass apparatus, 240 g of polyalcohol (OH number 359) in 50 g of toluene were reacted with 217 g of phosgene as in Example 1. The polyalcohol was used without dilution with a solvent. After reaction for 5 hours at 50° C., the mixture was stripped for 1 hour with nitrogen until it was phosgene-free. Then, in a 1l glass stirred flask, ammonia was introduced to saturation for 3 h at 25–30° C. As the ammonia was being introduced, a white precipitate formed. After the end of the reaction, the product was dissolved 1.3l of toluene and 250 ml of water. The water phase was separated off and the organic phase was washed with 250 ml of water. The organic phase was then concentrated on a rotary evaporator, giving 270 g of a pale brown solid with an OH number of 13. The IR spectrum showed the carbamate band as the sole functional group.

We claim:

1. A polycarbamate of the formula I

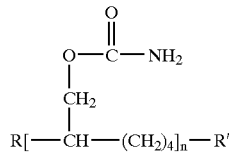

in which

R and R' are identical or different and are alkyl groups having 1–4 carbon atoms and n is a number from, on average, 2 to 5.

2. A polycarbamate as claimed in claim 1, which consists of a mixture of homologs where n=1 n=10.

3. A process for the preparation of polycarbamates of the formula I

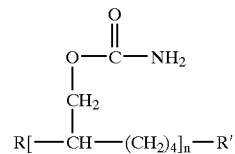

in which

R and R' are identical different and are alkyl groups having 1–4 carbon atoms and n is a number, on average, 2 to 5, which comprises reacting a polyalcohol of the formula II

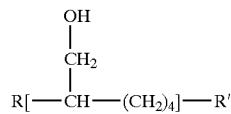

in which R, R' and n are as defined above, with phosgene to give a polychlorocarbonic ester of the formula III

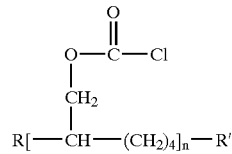

and then converting the polychlorocarbonic ester III into the polycarbamate I using ammonia.

4. A process as claimed in claim 3, wherein the reaction is carried out in an aprotic solvent.

5. A process as claimed in claim 3, wherein the reaction with phosgene is carried out at +5 to +65° C. and the reaction with ammonia is carried out at 5 to 50° C.

6. A method of use of the polycarbamates of the formula I as coating constituents, comprising the step of adding the polycarbamates to regulate the viscosity of the coatings.

7. A method of use as claimed in claim 6, wherein the coatings are automotives finishes.

* * * * *